United States Patent [19]
Conrad et al.

[11] 3,945,996
[45] Mar. 23, 1976

[54] ADDUCTS OF EPOXY COMPOUNDS AND PRODUCTS OF REACTION OF ε-CAPROLACTAM WITH N-ALKYLALKYLENEDIAMINE AND METHODS OF PREPARATION

[75] Inventors: Jens Conrad, Hilden; Hans Werner Eckert, Dusseldorf; Ferdi Saygin, Erkrath; Harald Schnegelberger, Leichlingen, all of Germany

[73] Assignee: Henkel & Cie GmbH, Dusseldorf-Holthausen, Germany

[22] Filed: Sept. 18, 1974

[21] Appl. No.: 507,045

[30] Foreign Application Priority Data
Sept. 24, 1973 Germany............................ 2347932

[52] U.S. Cl............ 260/239.3 R; 424/244; 424/204
[51] Int. Cl.²........................................ C07D 223/10
[58] Field of Search ............................ 260/239.3 R

[56] References Cited
FOREIGN PATENTS OR APPLICATIONS
55,547  11/1943  Netherlands................. 260/239.3 R Primary Examiner—John D. Randolph
Assistant Examiner—Robert T. Bond
Attorney, Agent, or Firm—Hammond & Littell

[57] ABSTRACT

A process for producing an addition product of an epoxy compound with a reaction product of ε-caprolactam and an N-alkylalkylene diamine, as well as the addition product produced by the process. The process of using these addition products is to prevent the growth of microorganisms in industrial water, by incorporating into said industrial water an antimicrobially effective amount of said addition product, and optionally incorporating into said industrial water a sequestering agent comprising a water-soluble phosphonic acid which forms a complex with a divalent metal, a water-soluble salt of the acid and the mixtures thereof, with the weight ratio of sequestering agent to addition product being 1:10 to 10:1.

11 Claims, No Drawings

ADDUCTS OF EPOXY COMPOUNDS AND PRODUCTS OF REACTION OF ε-CAPROLACTAM WITH N-ALKYLALKYLENEDIAMINE AND METHODS OF PREPARATION

THE PRIOR ART

Alkylamines and N-alkylalkylenediamines having alkyl of about 8 to 18 carbon atoms are well known in the literature as having antimicrobial activity. However, they possess detrimental dermatological and toxicological properties which prevent their practical use on a large scale. Moreover, they are unsuitable for technological use because they are highly toxic to fish.

A considerably better physiological compatibility is shown by the products of the reaction of ε-caprolactam with N-alkylalkylenediamines used in a molar ratio of amine: lactam of 1 : 1 to 1 : 10 and when the amines have an alkyl of 10 – 18 carbon atoms. The efficacy of such reaction products against gram-positive and gram-negative bacteria, fungi and algae is excellent. The preparation of these compounds and their special use for water conservation is disclosed in U.S. patent application Ser. No. 352,981 filed Apr. 20, 1973 (Eckert et al), now U.S. Pat. No. 3,892,806, and Ser. No. 352,941 filed Apr. 20, 1973 (Koppensteiner et al), now U.S. Pat. No. 3,874,869. However, these compounds are difficulty soluble and are not always dispersible to a sufficient extent in special systems, so that great difficulties for certain uses can occasionally arise. Moreover, a need has existed for a very effective, physiologically unobjectionable antimicrobial agent which at the same time, is readily soluble in aqueous systems; and therefore can be incorporated into many different systems.

OBJECT OF THE INVENTION

It is an object of the present invention to provide adducts of ethylene oxide, propylene oxide, or glycidol and products of the reaction of ε-caprolactam with N-alkylalkylenediamines, as well as a process of producing these adducts.

It is another object of the present invention to provide a composition and a process for using said adducts to prevent the growth of microorganisms, and preferably in industrial water.

These and further objects of the invention will become apparent as the description thereof proceeds.

DESCRIPTION OF THE INVENTION

The present invention concerns adducts of ethylene oxide, propylene oxide, or glycidol and products of the reaction of ε-caprolactam with N-alkylalkylenediamines, their preparation, and their use as antimicrobial agents.

It has now been found that the above objects of this invention are satisfied by adducts of ethylene oxide, propylene oxide, or glycidol and compounds which are obtained by the reaction of ε-caprolactam with N-alkylalkylenediamines having the formula

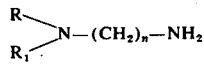

in which R designates a straight-chained or branch-chained, saturated or unsaturated, aliphatic hydrocarbon residue having 8 to 18 carbon atoms, $R_1$, designates hydrogen or an aliphatic hydrocarbon residue having 1 to 4 carbon atoms, $n$ is an integer from 2 to 6 preferably 3, and the molar ratio of the reaction component N-alkylalkylenediamine: reaction component ε-caprolactam is 1 : 1 to 1 : 10, the reaction of said diamine with said lactam being carried out for 3 to 20 hours at temperatures above 180°C, preferably at about 250°C, and the molar ratio of N-alkylalkylenediamine to the compound containing the epoxy group is 1 : 0.5 to 3, preferably, 1 : 1 to 2.

More particularly, the present invention provides an addition product of an epoxy compound selected from the group consisting of ethylene oxide, propylene oxide and glycidol with a reaction product of ε-caprolactam with an N-alkylalkylene diamine of the formula

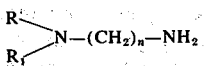

wherein R is selected from the group consisting of alkyl having 8 to 18 carbon atoms, hydroxyalkyl having 8 to 18 carbon atoms, alkenyl having 8 to 18 carbon atoms, hydroxyalkenyl having 8 to 18 carbon atoms, alkadienyl having 8 to 18 carbon atoms, alkatrienyl having 8 to 18 carbon atoms, and mixtures of alkyl derived from fatty acid mixtures having 8 to 18 carbon atoms, $R_1$ is a member selected from the group consisting of hydrogen and alkyl of 1 to 4 carbon atoms, and $n$ is an integer from 2 to 6, with the molar ratio of N-alkylalkylene diamine to ε-caprolactam ranging from 1:1 to 1:10, said reaction being carried out for 3 to 20 hours in the liquid phase at temperatures above 180°C to produce said reaction product, and then reacting said reaction product with said epoxy compound where the amount of epoxy compound is selected so that the molar ratio between the N-alkylalkylene diamine charged in said reaction product to said epoxy compound ranges from 1:0.5 to 3 at a temperature of between 50°C to 150°C for a time effective to product said addition product.

The present invention is also directed to the method of preparing the above-described addition product by first preparing the above-mentioned reaction product of ε-caprolactam with said N-alkylalkylene diamine, and then reacting said reaction product with an epoxy compound selected from the group consisting of ethylene oxide, propylene oxide and glycidol; and recovering said addition product.

The present invention is further directed to an antimicrobial and algicidal composition active against gram-positive bacteria, gram-negative bacteria, fungi and algae consisting of from 0.1 to 5% by weight based upon the total weight of the above-described addition product; and the remainder of an inert carrier.

The present invention also provides a process for the prevention of the growth of microorganisms selected from the group consisting of gram-positive bacteria, gram-negative bacteria, fungi and algae which consists essentially of contacting said microorganisms with an amount effective to prevent the growth of said microorganisms of the above-described addition product, and preferably in an industrial water or service water environment.

The preferred preparation of the products of the reaction of ε-caprolactam with N-alkylalkylenediamines, is carried out by heating a melted mixture of the reaction components as defined by the desired ratio and using a temperature above 180°C, preferably a temperature of about 250°C, and a reaction time of between 3 to 20 hours. By this method, the reaction products are obtained was water-clear, thinly liquid melts which are preferably used immediately following their preparation. Without any further purification these reaction products are caused to react with compounds containing epoxy groups to form the new products according to the invention.

The N-alkylalkylene diamines used as starting materials represent products that are known in the literature. They can be obtained, for example, by selective alkylation of corresponding diamines or by the reaction of alkyl amines with acrylonitrile and subsequent hydrogenation (Houben-Weyl, Methoden der Organischen, Chemie, 4th ed. vol. 11/1 p. 564; French patent 1,351,793). Of particular importance as starting amines are the N-alkyl-1,3-propylene diamines, since the reaction products with ε-caprolactam produced from them have particularly valuable properties, and these amines are, on the other hand, readily available. These readily available diamines are substantially those whose alkyl radicals are preferably straight-chained, saturated or unsaturated, and whose alkyl radicals originate from the corresponding fatty acids, for example alkanoic acids of 8 to 18 carbon atoms such as lauric acid, myristic acid, palmitic acid and stearic acid; for example hydroxyalkanoic acids of 8 to 18 carbon atoms such as hydroxystearic acid; alkenoic acids of 8 to 18 carbon atoms such as oleic acid and palmitoleic acid; hydroxyalkenoic acids of 8 to 18 carbon atoms such as ricinoleic acid; alkadienoic acids of 8 to 18 carbon atoms such as linoleic acid; alkatrienoic acids of 8 to 18 carbon atoms such as linolenic acid; and mixtures of fatty acids of 8 to 18 carbon atoms, as they are obtained, for example from coconut fatty acid, tallow fatty acid, soybean oil, linseed oil, palm oil, rape seed oil, colza oil, fish and whale oils, as well as their hydrogenation products.

As far as the antimicrobial action is concerned those addition reaction products which have proved particularly effective are those derived from N-alkylalkylene diamines of the above-mentioned formula, whose alkyl radical R contains 10 to 14 carbon atoms and wherein $R_1$ is hydrogen. Furthermore it was found advantageous as far as the antimicrobial action is concerned, if the molar ratio of N-alkylalkylene diamine to ε-caprolactam in these reaction products is preferably 1:1 to 1:5, and especially 1:1 to 1:3. As mentioned above, those addition reaction products which are of particular importance are those derived from N-alkylalkylene diamines, where $n = 3$; that is, from N-alkyl-1,3-propylene diamines, having the formula

wherein R has the above-defined meanings.

Suitable examples of reaction products for the addition of ethylene oxide, propylene oxide or glycidol include the reaction products of ε-caprolactam with the following N-alkylalkylene diamines in the indicated molar ratio:

N-dodecyl-1,2-ethylene diamine 5:1,
N-coconut fatty alkyl-1,2-ethylene diamine 3:1,
N-dodecyl-N-ethyl-1,3-propylene diamine 3:1,
N-decyl-1,4-butylene diamine 2:1,
N-tallow fatty alkyl-1,4-butylene diamine 10:1,
N-dodecyl-1,5-pentylene diamine 5:1,
N-tetradecyl-1,6-hexylene diamine 3:1 and
N-hexadecyl-1,6-hexylene diamine 4:1.

Preferred are those with N-decyl-1,3-propylene diamine 3:1,
N-dodecyl-1,3-propylene diamine 1:1,
N-dodecyl-1,3-propylene diamine 2:1,
N-dodecyl-1,3-propylene diamine 4:1,
N-dodecyl-1,3-propylene diamine 5:1,
N-coconut fatty alkyl-1,3-propylene diamine 3:1,
N-coconut fatty alkyl-1,3-propylene diamine 1:1,
N-coconut fatty alkyl-1,3-propylene diamine 2:1,
N-tetradecyl-1,3-propylene diamine 3:1,
N-hexadecyl-1,3-propylene diamine 3:1,
N-octadecyl-1,3-propylene diamine 3:1,
N-tallow fatty alkyl-1,3-propylene diamine 3:1 and
N-hardened tallow fatty alkyl-1,3-propylene diamine 3:1.

The above-named products of the reaction of ε-caprolactam with N-alkylalkylenediamine are further reacted with ethylene oxide, propylene oxide, or glycidol in a known manner using elevated temperatures ranging from 50° to 150°C. For the economical preparation of the addition products according to the invention, it has been found advantageous to carry out the addition reaction immediately after the products of the reaction of ε-caprolactam with N-alkylalkylenediamine have been prepared and to use them without further purification. The ratio of quantities of the reaction components is so chosen that the molar ratio of N-alkylalkylenediamine in the reaction product to ethylene oxide, propylene oxide, or glycidol is 1 : 0.5 to 3, preferably 1 : 1 to 2.

The addition products prepared according to the invention are colorless, pasty to highly viscous masses, which are satisfactorily soluble in water and in organic solvents, such as, for example, in alcohols, ketones, esters, and/or chlorinated hydrocarbons.

When equimolar amounts of acids, such as inorganic acids, for example sulfuric acid or phosphoric acid or such as organic acids for example formic acid, acetic acid, lactic acid, tartaric acid or citric acid are added after the reaction, it is possible to prepare the corresponding acid addition salts of the epoxy addition products according to the invention. These acid addition salts possess good water-solubility.

The addition products according to the invention show very good microbiostatic and microbiocidal activity with respect to gram-positive bacteria, gram-negative bacteria, fungi, and also show a good inhibitory effect upon algae. These addition products are excellently suitable for solving various technical problems of disinfection and conservation because of their excellent dermal tolerance and their very low toxicity. Examples for such potential applications are the use as disinfectants in household cleaners, in industrial cleaners for foodstuff factories, dairies, breweries, in disinfectants for hospital areas; the use for disinfection in customary laundry processes and in dry-cleaning; the use as preservative for cosmetics and adhesives based on cellulose, starch, and animal protein; the use as preservative for dispersion dye-stuffs, metal-working oils, and service water for many different purposes, such as for example, in coolant circuits, swimming poools, scrubbers for air conditioning installations and another example is the use as a deodorant in deodorant soaps.

For use as antimicrobial agents, the epoxy addition products according to the invention can be incorporated into liquid, pasty, or solid preparations. For this application, the amount of these products used may vary from 0.1% to 5% by weight, preferably 0.5% to 3% by weight based on the total weight. For use in the preservation of industrial water, an amount is used such that 0.5 to 50 mgm, preferably 1 to 10 mgm, of an epoxy addition product according to the invention is charged per liter of the industrial water or service water to be treated. When the substances according to the invention are to be packaged for the various applications, they can be combined with other additives, such as surface-active agents, water softeners, rust preventatives, complex-formers, thickeners, bases, acids, perfumes, foam inhibitors, solvents and others.

The addition products according to the invention for the preservation of industrial water and service water are advantageously utilized in combination with phosphonic acids or their water-soluble salts serving as sequestering agents, or complex-forming materials.

Preferred are the phosphonic acids which form complexes with divalent metals, and having the following formulae:

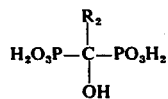
$$H_2O_3P-\underset{\underset{OH}{|}}{\overset{\overset{R_2}{|}}{C}}-PO_3H_2 \qquad (I)$$

in which $R_2$ represents phenyl or alkyl of 1 to 5 carbon atoms;

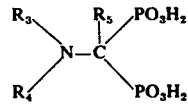
$$\underset{R_4}{\overset{R_3}{\diagdown}}N-\underset{\underset{PO_3H_2}{|}}{\overset{\overset{R_5}{|}}{C}}\diagup^{PO_3H_2} \qquad (II)$$

in which $R_3$ and $R_4$ each represent hydrogen or alkyl of 1 to 4 carbon atoms, $R_5$ represents hydrogen, alkyl of 1 to 4 carbon atoms, or phenyl;

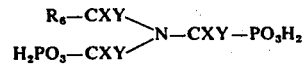
$$\underset{H_2PO_3-CXY}{\overset{R_6-CXY}{\diagdown}}N-CXY-PO_3H_2 \qquad (III)$$

in which X and Y each represent hydrogen or an alkyl of 1 to 4 carbon atoms, $R_6$ represents —$PO_3H_2$ or a group of the formula:

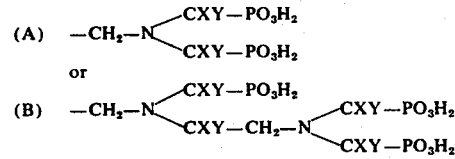

(A) $-CH_2-N\diagup^{CXY-PO_3H_2}_{CXY-PO_3H_2}$ or (B) $-CH_2-N\diagup^{CXY-PO_3H_2}_{CXY-CH_2-N\diagup^{CXY-PO_3H_2}_{CXY-PO_3H_2}}$ in which X and Y each have the above-defined meaning; and

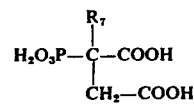
$$H_2O_3P-\underset{\underset{CH_2-COOH}{|}}{\overset{\overset{R_7}{|}}{C}}-COOH \qquad (IV)$$

in which $R_7$ represents hydrogen, methyl or —$CH_2$—$CH_2$—COOH.

Suitable examples of 1-hydroxyalkane-1,1-diphosphonic acids of formula I which may be used are 1-hydroxyethane-1,1-diphosphonic acid, 1-hydroxypropane-1,1-diphosphonic acid, 1-hydroxybutane-1,1-diphosphonic acid, 1-hydroxypentane-1,1-diphosphonic acid, 1-hydroxyhexane-1,1-diphosphonic acid, as well as 1-hydroxy-1-phenylmethane-1,1-diphosphonic acid; and the 1-hydroxyethane-1,1-diphosphonic acid is preferred. Suitable examples of 1-aminoalkane-1,1-diphosphonic acids of formula II are 1-aminoethane-1,1-diphosphonic acid, 1-amino-1-phenylmethane-1,1-diphosphonic acid, 1-dimethylaminoethane-1,1-diphosphonic acid, 1-dimethylaminobutane-1,1-diphosphonic acid, 1-diethylaminomethane-1,1-diphosphonic acid, 1-propylaminomethane-1,1-diphosphonic acid, and 1-butylaminomethane-1,1-diphosphonic acid.

Suitable examples of aminopolymethylene phosphonic acids of the formula III include aminotrimethylenephosphonic acid, ethylenediaminotetramethylenephosphonic acid, diethylenetriaminopentamethylenephosphonic acid, aminotri(2-propylene-2-phosphonic acid).

Suitable examples of phosphono succinic acids of formula IV include phosphonosuccinic acid, 1-phosphono-1-methylsuccinic acid and 2-phosphonobutane-1,2,4-tricarboxylic acid.

Instead of the phosphonic acids mentioned above, their water-soluble salts may also be used, such as alkali metal salts especially the sodium salt or potassium salt, as well as the ammonium salts, or the lower alkanolamine salts, for example triethanolamine salt. The phosphonic acids or their water-soluble salts may be used singly or in mixtures thereof. Particularly suitable is a mixture of 1-hydroxyethane-1,1-diphosphonic acid and aminotrimethylene phosphonic acid in a weight ratio of 4:1 to 1:4.

The phosphonic acids or their water-soluble salts are added to the antimicrobial agents in such an amount that these agents contain per liter of the industrial water or service water to be treated from 0.2 mgm up to 1.5 times the amount that is necessary for the complete sequestration of the hardness former ions found in the treated water.

It has been found that the above described combination of the phosphonic acid component with the biocide component has a number of advantages. The weight ratio between the phosphonic acid component and biocide component can vary between 1:10 and 10:1. Preferably, however, a weight ratio of 3:1 to 1:3 is used. The water to be treated with the agents according to the invention should have a content of phosphonic acid between 0.2 and 20 gm/m³ and a content of biocide between 0.5 and 50 gm/m³.

Suitable corrosion inhibitors include water-soluble orthophosphates, for example mono-, di- or trialkali metal orthophosphates. Furthermore water-soluble zinc salts, for example zinc sulfate or zinc nitrate can be used, which are added instead of the orthophosphates, but perferably simultaneously with the orthophosphates. Other inhibitors which can be added, if desired, are alkali metal nitrites, such as potassium nitrite or particularly sodium nitrite. An addition of alkali metal silicates, such as potassium silicate or sodium silicate is also possible. The inhibitors are added in amounts of from 0.5 to 200 mgm/liter, preferably 1 to 50 mgm/liter. The individual additives can be processed into solid mixtures. But it is also possible to produce solutions therefrom which are then added to the water in the desired amount. It is also possible to regulate the pH of these products, either by adding an alkali metal hydroxide, such as sodium hydroxide, or by selecting a suitable mono-, di-, or tri-alkali metal orthophosphate, so that a certain pH range of the treated water can be achieved at the same time.

The unexpected advantages of the combination of the above described biocides with the phosphonic acid components consist among others in the increased synergistic attack of the biocide on the biological material and the microorganisms. This leads to a very rapid degradation of their growth. The dispersing action of the phosphonic acids as well as their corrosion and rust preventative effects are reciprocally enhanced by the biocide components. Due to the very low dosages both of the phosphonic acid component and of the biocide component, the outlet drain emits a minimum amount of these components. Due to the absorption of the biocide component by the biological material, the content of harmful substances discharged by the outlet drain is further decreased. In addition, the biocide component is biologically degradable after being discharged and correspondingly diluted.

The following examples are merely illustrative of the present invention without being deemed limitative in any manner thereof.

EXAMPLE 1

For the tests of antimicrobial and algicidal activity a series of addition products according to the invention was prepared by the following process. A mixture of ε-caprolactam and N-alkyl-1,3-propanediamine in the intended mol ratio was heated to 250°C and stirred vigorously under an atmosphere of dried nitrogen. The mixture was then left standing at this temperature for 3 to 20 hours. After the reaction had been completed, the resulting water-clear thinly liquid melt was cooled to 150°C transferred to an autoclave, reacted with the intended amount of ethylene oxide or propylene oxide at 100°C to 130°C, and after further stirring for 2 to 3 hours at this temperature, the reaction mixture was allowed to cool.

In the case of reaction with glycidol, the melt was cooled to 80°C reacted with the intended amount of glycidol within 30 to 60 minutes, while keeping the temperature from exceeding 85°C. Then, stirring was continued at 80°C for 2 hours, followed by cooling.

The addtion products thus prepared are colorless, pasty masses.

In the following Table I, the products thus prepared are characterized by their alkyl residue; the ratio of N-alkyl-1,3-propylenediamine to ε-caprolactam; the reaction time for the preparation of the reaction product; the number of mols of ethylene oxide (EO), propylene oxide (PO), or glycidol (G) per mol of N-alkylalkylenediamine; and the % nitrogen in the product.

TABLE I

| Compound | Alkyl | N-Alkyl-1,3-Propylenediamine ε-Caprolactam Ratio | Reaction Time Hours | Mol Epoxy Compound per Mol Amine | $N_{Tur.}$ % |
|---|---|---|---|---|---|
| A | Decyl | 1:3 | 20 | 1 Mol EO | 4.45 |
| B | Dodecyl | 1:1 | 5 | 1 Mol PO | 6.55 |
| C | Dodecyl | 1:1.5 | 5 | 1 Mol G | 5.50 |
| D | Dodecyl | 1:2 | 5 | 1 Mol EO | 4.88 |
| E | Dodecyl | 1:2 | 5 | 2 Mol EO | 4.63 |
| F | Dodecyl | 1:2 | 5 | 3 Mol EO | 4.29 |
| G | Dodecyl | 1:2 | 5 | 1 Mol PO | 4.61 |
| H | Dodecyl | 1:2 | 5 | 2 Mol PO | 4.32 |
| J | Dodecyl | 1:2 | 5 | 3 Mol PO | 3.94 |
| K | Dodecyl | 1:2 | 5 | 1 Mol G | 4.40 |
| L | Dodecyl | 1:2 | 5 | 2 Mol G | 3.68 |
| M | Dodecyl | 1:2 | 5 | 3 Mol G | 3.30 |
| N | Dodecyl | 1:3 | 5 | 1 Mol EO | 4.39 |
| O | Dodecyl | 1:3 | 5 | 2 Mol EO | 4.10 |
| P | Dodecyl | 1:3 | 5 | 1 Mol PO | 4.28 |
| Q | Dodecyl | 1:3 | 5 | 2 Mol PO | 4.22 |
| R | Dodecyl | 1:3 | 5 | 3 Mol PO | 4.06 |
| S | Dodecyl | 1:3 | 5 | 1 Mol G | 4.10 |
| T | Dodecyl | 1:3 | 5 | 2 Mol G | 3.79 |
| U | Dodecyl | 1:3 | 5 | 3 Mol G | 3.39 |
| V | Dodecyl | 1:5 | 20 | 0.5 Mol EO | 3.26 |
| W | Coconut Fatty alkyl | 1:3 | 20 | 1 Mol EO | 4.19 |
| X | Tetradecyl | 1:3 | 20 | 1 Mol PO | 4.20 |
| Y | Tallow Fatty alkyl | 1:3 | 20 | 1 Mol EO | 3.41 |

EXAMPLE 2

The antimicrobial activity of adducts of epoxy compounds and the reaction products of ε-caprolactam with N-alkyl-1,3-propylenediamines listed in Table I above was determined by measuring each product's inhibiting effect on the following test bacteria, fungi and organisms in contaminated industrial water;

1. *Staphylococcus aureus* $5 \times 10^7$ organisms per ml
2. *Escherichia coli* $4 \times 10^7$ organisms per ml
3. *Pseudomonas aeruginosa* $4 \times 10^7$ organisms per ml
4. *Candida albicans* $2 \times 10^6$ organisms per ml
5. *Aspergillus niger* $9 \times 10^5$ organisms per ml
6. *Aerobacter aerogenus* $5 \times 10^7$ organisms per ml
7. *Fusarium spec.* $2 \times 10^4$ organisms per ml
8. Mixture of contaminated industrial water from 3 cooling towers
9. Mixture of contaminated industrial water from 3 wash towers of air conditioning installations.

The inhibiting concentrations of the individual substances were determined using the so-called dilution test for determining the microbiostatic effect as described in the method for testing chemical disinfectants by the German Society for Hygiene and Microbiology (1959), under the methods of preliminary evaluations of such materials, and can be used to advantage in different tests not utilizing the liquid nutrient media stated in the said directives. The advantage of solid nutrient media is obvious, particularly when testing the efficacy of substances with respect to fungi.

The tests were carried out in test tubes which were filled with Merck Standard I broth or with beer wort (8° Be) in a dilution of 1:5 with tap water. After adding the active substance, the nutrient solution volume in the test tube was 10 ml. Subsequently the tubes were inoculated with 0.1 ml of the test organism suspension. The inoculated tubes were incubated in the case of bacteria for 3 days at 37°C and in the case of fungi for 6 days at 30°C in the incubator. Subsequently it was determined which substance concentration added to the nutrient medium could just inhibit completely the growth of the germs. This value was called the minimum inhibiting concentration. The tests were carried out with the following concentration levels; and the results were compiled below in Table II as follows: 5,000 ppm, 2,500 ppm, 1,000 ppm, 750 ppm, 500 ppm, 250 ppm, 100 ppm, 50 ppm, 25 ppm, 10 ppm, 7.5 ppm, 5 ppm, 2.5 ppm, and 1 ppm.

pipetted into test tubes at a temperature of 18°C to 21°C.
1. Staphylococcus aureus 5 × $10^7$ organisms per ml
2. Escherichia coli 4 × $10^7$ organisms per ml
3. Pseudomonas aeruginosa 4 × $10^7$ organisms per ml Each 0.1 ml portion of the above test organism suspensions was diluted to 10 ml with tap water containing the products of the invention to be tested (16° German hardness). The concentrations of the products according to the invention were 100 ppm, 250 ppm and 500 ppm in each case. After reaction times of 1, 2.5, 5, 10, 20, 30 and 60 minutes a dropper-full of material was taken from the test tubes and pipetted into 10 ml nutrient solution which contained 3% Tween 80 and 0.3% lecithin as de-inhibitors. The nutrient solutions inoculated with bacteria were incubated at 37°C while those inoculated with fungi were incubated at 30°C in an incubator. After 6 days the cultures were evaluated macroscopically for growth of the test organisms; and the sterilization times were then determined. The results are complied in Table III.

TABLE II

Inhibiting concentrations in ppm for Compound A to Y

| Compound | Test organism or test product used | | | | | | | | |
|---|---|---|---|---|---|---|---|---|---|
| | 1 | 2 | 3 | 4 | 5 | 6 | 7 | 8 | 9 |
| A | 50 | 25 | 100 | 250 | 250 | 25 | 100 | 25 | 25 |
| B | 10 | 10 | 25 | 50 | 50 | 10 | 10 | 5 | 5 |
| C | 10 | 10 | 25 | 100 | — | 25 | 25 | 10 | 10 |
| D | 10 | 10 | 25 | 50 | 50 | 10 | 25 | 7.5 | 7.5 |
| E | 50 | 50 | 50 | 250 | 100 | 25 | 50 | 10 | 10 |
| F | 50 | 50 | 100 | 250 | 100 | 50 | 50 | 25 | 25 |
| G | 5 | 5 | 100 | 50 | 50 | 10 | 10 | 7.5 | 7.5 |
| H | 10 | 5 | 100 | 250 | — | 10 | 25 | 10 | 10 |
| J | 50 | 50 | 250 | 500 | — | 50 | 25 | 10 | 10 |
| K | 10 | 10 | 50 | 100 | 100 | 25 | 25 | 10 | 10 |
| L | 50 | 10 | 250 | 250 | — | 100 | 50 | 25 | 25 |
| M | 100 | 50 | 500 | 250 | — | 100 | 250 | 50 | 50 |
| N | 50 | 10 | 50 | 50 | 100 | 50 | 50 | 10 | 10 |
| O | 50 | 50 | 100 | 100 | 250 | 100 | 50 | 25 | 25 |
| P | 10 | 10 | 100 | 100 | 100 | 50 | 25 | 10 | 10 |
| Q | 50 | 50 | 500 | 250 | 100 | 50 | 50 | 10 | 25 |
| R | 50 | 10 | 500 | 250 | 250 | 100 | 100 | 25 | 25 |
| S | 10 | 10 | 50 | 100 | 250 | 100 | 50 | 10 | 10 |
| T | 50 | 50 | 250 | 250 | — | 250 | 50 | 25 | 25 |
| U | 100 | 50 | 1000 | 250 | — | 250 | 250 | 50 | 50 |
| V | 10 | 25 | 100 | 500 | — | 25 | 25 | 10 | 10 |
| W | 25 | 50 | 250 | 100 | 100 | 25 | 50 | 25 | 25 |
| X | 10 | 50 | 100 | 100 | — | — | 50 | 50 | 50 |
| Y | 50 | 100 | 500 | 250 | 500 | — | — | 100 | 100 |

The "—" sign indicates that no tests were conducted. This table shows the unexpectedly superior inhibiting effect of the active substances according to the invention on bacteria and fungi.

EXAMPLE 3

The microbiocidal activity of some of the addition products listed in Example 1 was determined by means of the suspension test. The procedure for this testing method is described in the method for the testing of chemical disinfectants published by the German Society for Hygiene and Microbiology (1959), under the methods of preliminary evaluations of such materials. According to these procedures 0.1 ml test organism suspension of the following bacteria and fungi were

TABLE III

Sterilization times of the products according to the invention with regard to the various test organisms, in minutes:

| | | Concentration of the Products in Tap Water | | |
|---|---|---|---|---|
| Compound | Organism | 100 ppm | 250 ppm | 500 ppm |
| D | 1 | 5 | 2.5 | 2.5 |
| | 2 | — | — | — |
| | 3 | 40 | 40 | 10 |
| G | 1 | 2.5 | 2.5 | 2.5 |
| | 2 | 5 | 5 | 2.5 |
| | 3 | 10 | 5 | 2.5 |
| K | 1 | 2.5 | 2.5 | 2.5 |
| | 2 | 20 | 5 | 5 |
| | 3 | 10 | 5 | 5 |
| N | 1 | 5 | 2.5 | 2.5 |
| | 2 | 60 | 10 | 5 |
| | 3 | >120 | 40 | 10 |
| P | 1 | 2.5 | 2.5 | 2.5 |
| | 2 | 2.5 | 2.5 | 2.5 |
| | 3 | 10 | 5 | 5 |

The "—" indicates that no tests were conducted.

The foregoing table clearly indicates the unexpectedly superior sterilization activity of the addition products according to the invention with regard to gram-positive bacteria and gram-negative bacteria.

EXAMPLE 4

The inhibiting activity on algae was determined in cylindrical vessels under intensive aeration. Into the vessels were charged 100 ml of a nutrient solution mixed with increasing amounts of active substances and 4 ml of a mixed suspension of *Scenedesmus obliquus* and *Chlorella vulgaris*.

The nutrient solution had the following composition:

| | | |
|---|---|---|
| ammonium chloride | 0.1 | gm |
| sodium nitrate | 1.0 | gm |
| dipotassium hydrogen phosphate | 0.25 | gm |
| crystalline magnesium sulfate | 0.5 | gm |
| calcium chloride | 0.1 | gm |
| ferric chloride | 0.003 | gm | per 1,000 ml of distilled water. The pH of the nutrient solution was 7.2. The tests were carried out with the following concentration levels of active substance: 10 ppm, 5 ppm, 2.5 ppm, 2 ppm, 1.5 ppm, 1 ppm, 0.75 ppm, 0.5 ppm and 0.25 ppm. The minimum inhibiting concentrations determined in the tests after 7 days were compiled in Table IV.

TABLE IV

| Compound | Inhibition of the algae growth Inhibiting concentration in ppm |
|---|---|
| B | 0.75 |
| D | 1 |
| E | 1.5 |
| G | 1 |
| K | 2.5 |
| N | 1.5 |
| P | 1 |
| W | 2.5 |
| X | 5 |

Thus Table IV indicates that the active substances according to the invention have an unexpectedly superior inhibiting activity on the growth of algae.

EXAMPLE 5

Inhibition of the growth of sulfate-reducing bacteria

The inhibiting concentrations were determined in 50 ml bottles provided with a screwcap. The bottles were charged with an optimum nutrient solution for the growth of sulfate-reducing bacteria of the following composition:

| | |
|---|---|
| Sodium lactate | 4.0 gm |
| Yeast extract | 1.0 gm |
| Ascorbic acid | 0.1 gm |
| Crystalline magnesium sulfate | 0.5 gm |
| Dipotassium hydrogen phosphate | 0.2 gm |
| Ammonium ferric alum | 0.1 gm |
| Sodium chloride | 2 gm | per 1,000 ml of distilled water. The pH of the nutrient solution was 7.4. After adding the active substances to be tested in the various concentrations, the mixture was inoculated with 1 ml of a pure culture of Desulfovibrio desulfuricans $6 \times 10^5$ organisms per ml and then incubated for 4 weeks at 37°C in an incubator. The tests were carried out with the following concentrations levels: 100 ppm, 50 ppm, 40 ppm, 30 ppm, 20 ppm, 10 ppm, 5 ppm, 2.5 ppm and 1 ppm.

In this test the following minimum inhibiting concentrations were determined for the various addition products of the invention; and the results were compiled in Table V.

TABLE V

| Compound | Inhibition of the growth of desulfovibrio desulfuricans Inhibiting concentration in ppm |
|---|---|
| B | 2.5 |
| D | 5 |
| E | 10 |
| G | 2.5 |
| K | 10 |
| N | 10 |
| W | 20 |

This test indicates the unexpectedly superior activity of the substances according to the invention as regarding inhibiting the growth of sulfate-reducing bacteria.

EXAMPLE 6

The cooling cycle of a steam power plant with a volume of 6,000 m³ and an hourly supply of 150 m³, as well as a circulation of 11,000 m³/h having about 3-fold concentration was treated for 6 months with a mixture of 1-hydroxyethane-1,1-diphosphonic acid and aminotrimethylene phosphonic acid in a weight ratio of 1:1. The amount of the mixture added was 4 gm/m³. Despite a good anticorrosive action and the prevention of boiler scale calcium deposition, serious difficulties always occurred and resulted from the growth on the condenser of slime-forming bacteria. Consequently an additional dose of 5 gm/m³ of a product of the addition of 1 mol ethylene oxide to a product prepared by the reaction of N-dodecyl-1,3-propylenediamine with ε-caprolactam in a molar ratio of 1:2 (Product D). When this combination of an addition product of the invention and the phosphonic acids were added, the difficulties in the coolant circuit were completely removed by their combined activity. There was no increase in the degree of hardness of the coolant water, and there was no bacterial growth.

EXAMPLE 7

In order to demonstrate that the addition products according to the invention possess good physiological compatability as compared with N-alkylalkylenediamines, the toxicological properties of the following products were tested:

Prior art product: Dodecyl-1,3-propylenediamine
Product D in Table I: Product of addition of 1 mol ethylene oxide to 1 mol of a product prepared by the reaction of dodecyl-1,3-propylenediamine with ε-caprolactam in a mole ratio of 1:2.

The following details of the tests conducted are reported:

1. The dermal tolerance of the hairless mouse was determined by treatment with 1% preparations in olive oil. (10 animals).
2. The mucocutaneous tolerance of the eye of the rabbit was determined by treatment with 1% preparations in olive oil.
3. For determination of the fish toxicity $LC_o$, "Goldorfen" (*Idus idus melanotus* Heck) was chosen.

The results obtained in these tests were reported in the following Table VI.

TABLE VI

Results of the Toxicological Tests

| Test No. | Prior Art Product | Product D |
|---|---|---|
| 1 | 5 Treatments (once daily) gave the following results:<br>2 Skin spots, light irritations<br>3 Skin spots, distinct irritations<br>2 Skin spots with strong weeping eczema | 10 Treatments (twice daily) gave the following results:<br>All animals, no findings of skin irritation. |
| 2 | Heavy conjunctival reaction which even after 8 days had not entirely attenuated; medium strong irritations of cornea and iris. | Slight conjunctival reaction after 2 hours, was not detectable after 6 hours. |
| 3 | 0.15 ppm | 1.5 ppm |

The results in Table VI indicate the unexpectedly superior physiological compatability of the products according to the invention.

The following examples illustrate further utility for the addition products according to the invention without being deemed limitative in any manner thereof.

EXAMPLE 8

Preparation of a Packaged Addition Product

Under an inert nitrogen atmosphere, 242 gm (1 mol) of N-dodecyl-1,3-propylenediamine and 226 gm (2 mols) of $\epsilon$-caprolactam were stirred at 230°C – 250°C for 5 hours. Then, the melt which had been cooled to 150°C was emptied into an autoclave; 44 gm (1 mol) of ethylene oxide were added at 100°C – 130°C and stirring was continued at this temperature for additional 2 to 3 hours. After the melt had been cooled to 100°C it was drawn off and upon further cooling, a colorless, pasty mass resulted. Into 100 parts by weight of the melt which had been cooled to about 80°C, 25 parts by weight of glacial acetic acid were stirred therein in such a manner that the temperature did not exceed 100°C. After the total amount of acetic acid had been added, 275 parts of de-ionized water were added. The resulting pale-yellow solution was suitable as stock solution for incorporation into various products.

EXAMPLE 9

Prewashing Agent with Simultaneous Antimicrobial Activity

A preliminary washing agent having antimicrobial activity was prepared from the following recipe by known procedures:

8.0 parts by weight of olefinsulfonate,
4.0 parts by weight of soap,
0.3 parts by weight of foam inhibitor,
36.0 parts by weight of $Na_4P_2O_7$,
7.5 parts by weight of NaOH,
10.2 parts by weight of $Na_2SO_4$, and
4.0 parts by weight of Addition Product D.

EXAMPLE 10

Antimicrobial Detergent for Laundries

An antimicrobial detergent for laundries was prepared from the following recipe by known procedures:
25 parts by weight of fatty alcohol sulfate,
35 parts by weight of $Na_5P_3O_{10}$,
7 parts by weight of $Na_2CO_3$,
15 parts by weight of $Na_2SO_4$,
5 parts by weight of $Na_2O$ — 3.3 $SiO_2$,
1 part by weight of carboxymethyl cellulose,
2 parts by weight of Addition Product B, and
10 parts by weight of pentasodium aminotrimethylene phosphonate.

EXAMPLE 11

Antimicrobial Acidic Detergent for the Beverage Industry

An antimicrobial acidic detergent for the beverage industry was prepared from the following recipe by known procedures:

| | |
|---|---|
| Phosphoric acid (80%) | 50 parts by weight, |
| Nonylphenol + 9 EO | 4 parts by weight, |
| 1-Hydroxyethane-1,1-diphosphonic Acid | 5 parts by weight, |
| Addition Product G | 1 part by weight, and |
| Water | 40 parts by weight. |

EXAMPLE 12

Antimicrobial Light Duty Detergent

An antimicrobial light duty detergent was prepared from the following recipe by known procedures:

| | | |
|---|---|---|
| Dodecylbenzene sulfonate | 30.0 | parts by weight, |
| Toluene sulfonate | 2.0 | parts by weight, |
| Sodium Coco-Fatty Alcohol Sulfate | 8.0 | parts by weight, |
| Sodium Sulfate | 30.0 | parts by weight, |
| Sodium Carboxymethyl Cellulose | 1.0 | parts by weight, |
| Addition Product K | 4.0 | parts by weight, and |
| Water | 25.0 | parts by weight. |

The addition products according to the invention can be also used as antimicrobial substances in dry-cleaning mixtures based on organic solvents having a small content of water. For the addition to the cleaning mixtures of the addition products A to Y, concentrations of 1 to 10 gm/liter are used. Customarily, the activators of the cleaning power based on anionic or non-ionic surface-active agents are added in the form of concentrates which contain not only the surface-active agents but also contain solvents such as chlorinated hydrocarbons or mineral oil and, if necessary, dissolving intermediaries, such as, for example, isopropanol and water. The addition products of the invention can be incorporated into these concentrates and dosed together with the activator for the cleaning power. In dry-cleaning, so much water is added to the cleaning mixtures that during the cleaning process, the relative humidity in the steam space over the mixture amounts to at least 70%.

The addition products of the invention can be not only used in detergents to obtain antimicrobial activity of the detergents, but can also be utilized as preservatives for cosmetics, starch pastes, glues, dispersion dyestuffs, cutting and boring oils, and the like.

For this purpose, an addition of 0.1% to 2% by weight, based on the product to be preserved, is generally sufficient.

EXAMPLE 13

An important field of application for the addition products according to the invention is in the conservation of industrial water and process water. An additive suitable for this purpose has the following composition:

| | |
|---|---|
| Stock solution of the acetate of Product D prepared using a procedure analogous to that described in Example 8 | 300 parts by weight, |
| Sodium salt of 1-hydroxyethane-1,1-diphosphonic acid | 15 parts by weight, |
| Sodium salt of aminotrimethylene phosphonic acid | 15 parts by weight, and |
| De-ionized water | |
| was added to produce a total of 1000 parts by weight. | |

100 cm$^3$ of this solution is used per m$^3$ of the industrial water to be preserved, such as, for instance, the cooling water for cooling towers of air conditioners.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. An addition product of an epoxy compound selected from the group consisting of ethylene oxide, propylene oxide and glycidol with a reaction product of ε-caprolactam with an N-alkylalkylenediamine of the formula

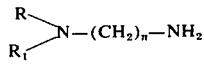

wherein R is selected from the group consisting of alkyl having 8 to 18 carbon atoms, hydroxyalkyl having 8 to 18 carbon atoms, alkenyl having 8 to 18 carbon atoms, hydroxyalkenyl having 8 to 18 carbon atoms, alkadienyl having 8 to 18 carbon atoms, alkatrienyl having 8 to 18 carbon atoms, and mixtures of alkyl derived from fatty acid mixtures having 8 to 18 carbon atoms, $R_1$ is a member selected from the group consisting of hydrogen and alkyl of 1 to 4 carbon atoms, and n is the integer 3, with the molar ratio of N-alkylalkylenediamine to ε-caprolactam ranging from 1:1 to 1:10, said reaction being carried out for 3 to 20 hours in the liquid phase at temperatures above 180°C to produce said reaction product, and then reacting said reaction product with said epoxy compound where the amount of epoxy compound is selected so that the molar ratio between the N-alkylalkylene diamine charged in said reaction product to said epoxy compound ranges from 1:0.5 to 3 at a temperature of between 50°C to 150°C for a time effective to produce said addition product.

2. The addition product of claim 1, in which R is alkyl having 10 to 14 carbon atoms, $R_1$ is hydrogen; the molar ratio of N-alkylalkylenediamine to ε-caprolactam is from 1:1 to 1:5; said reaction is conducted at about 250°C, and the molar ratio of N-alkylalkylenediamine to said epoxy compound is from 1:1 to 2.

3. The addition product of claim 2, in which the molar ratio of N-alkylalkylenediamine to ε-caprolactam is from 1:1 to 1:3.

4. An addition product of an epoxy compound selected from the group consisting of ethylene oxide, propylene oxide and glycidol with a reaction product of ε-caprolactam with N-alkyl-1,3-propylenediamines of the formula RHN — (CH$_2$)$_3$ — NH$_2$, wherein R is selected from the group consisting of alkyl having 8 to 18 carbon atoms, hydroxyalkyl having 8 to 18 carbon atoms, alkenyl having 8 to 18 carbon atoms, hydroxyalkenyl having 8 to 18 carbon atoms, alkadienyl having 8 to 18 carbon atoms, alkatrienyl having 8 to 18 carbon atoms, and mixtures of alkyl derived from fatty acid mixtures having 8 to 18 carbon atoms; with the molar ratio of N-alkyl-1,3-propylenediamine to ε-caprolactam ranging from 1:1 to 1:5, and said reaction is carried out for 3 to 20 hours in the liquid phase at a temperature above 180°C to produce said reaction product; and then reacting said reaction product with said epoxy compound where the amount of epoxy compound is selected so that the molar ratio between the N-alkylalkylenediamine charged in said reaction product to said epoxy compound ranges from 1:0.5 to 3 at a temperature of between 50°C to 150°C for a time effective to produce said addition product.

5. The addition product of claim 4, in which R is alkyl having 10 to 14 carbon atoms, said molar ratio of N-alkyl1,3-propylenediamine to ε-caprolactam ranging from 1:1 to 1:3; and said reaction being carried out at about 250°C.

6. The addition product of claim 4, in which R is selected from the group consisting of decyl, dodecyl, coconut fatty alkyl, tetradecyl, hexadecyl, tallow fatty alkyl, hardened tallow fatty alkyl, and octadecyl.

7. A method for the preparation of an addition product according to claim 1 consisting essentially of reacting ε-caprolactam with an N-alkylalkylenediamine of the formula

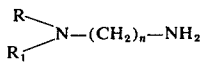

wherein R is selected from the group consisting of alkyl having 8 to 18 carbon atoms, hydroxyalkyl having 8 to 18 carbon atoms, alkenyl having 8 to 18 carbon atoms, hydroxyalkenyl having 8 to 18 carbon atoms, alkadienyl having 8 to 18 carbon atoms, alkatrienyl having 8 to 18 carbon atoms, and mixtures of alkyl derived from fatty acid mixtures having 8 to 18 carbon atoms, $R_1$ is a member selected from the group consisting of hydrogen and alkyl of 1 to 4 carbon atoms, and n is the integer 3 in a molar ratio of 1:1 to 1:10 for 3 to 20 hours in the liquid phase at a temperature above 180°C to produce a reaction product; reacting said reaction product with an epoxy compound selected from the group consisting of ethylene oxide, propylene oxide and glycidol where the amount of epoxy compound is selected so that the molar ratio between the N-alkylalkylenediamine charge in said reaction product to said epoxy compound ranges from 1:0.5 to 3 at a temperature of between 50°C to 150°C for a time effective to produce said addition product; and recovering said addition product.

8. The method of claim 7, in which the reaction is effected in the melt at about 250°C; in which the molar ratio of N-alkylalkylenediamine to ε-caprolactam is 1:1 to 1:5; in which the molar ratio of N-alkylalkylenediamine to epoxy compound is 1:1 to 2; and in which R is alkyl having 10 to 14 carbon atoms.

9. The method of claim 7, in which said molar ratio of N-alkylalkylenediamine to ε-caprolactam ranges from 1:1 to 1:3.

10. The method of claim 7, in which said N-alkylalkylenediamine has the formula $RHN-(CH_2)_3-NH_2$ in which R has the above assigned meaning, with the molar ratio of said diamine to ε-caprolactam of 1:1 to 1:5.

11. The method of claim 10, in which said molar ratio is 1:1 to 1:3; and in which said reaction is carried out at about 250°C.

* * * * *